(12) United States Patent
Stess et al.

(10) Patent No.: US 6,533,971 B1
(45) Date of Patent: Mar. 18, 2003

(54) CUSTOM MOLDED ORTHOPEDIC IMPRESSION SHIRT, KIT AND METHOD

(75) Inventors: Richard M. Stess, San Anselmo, CA (US); Peter M. Graf, San Francisco, CA (US)

(73) Assignee: Synthetic Tubular Socks, Inc., Mill Valley, CA (US)

( * ) Notice: Subject to any disclaimer, the term of this patent is extended or adjusted under 35 U.S.C. 154(b) by 133 days.

(21) Appl. No.: 09/660,310

(22) Filed: Sep. 12, 2000

(51) Int. Cl.[7] ............................................. B29C 33/38
(52) U.S. Cl. ..................................... 264/40.1; 264/222
(58) Field of Search ................................ 264/222, 40.1

(56) References Cited

U.S. PATENT DOCUMENTS

| | | | |
|---|---|---|---|
| 2,847,061 A | * | 8/1958 | Morton .................. 297/452.28 |
| 3,599,962 A | * | 8/1971 | Henry ........................ 269/182 |
| 3,656,475 A | | 4/1972 | Hanrahan, Jr. |
| 4,019,506 A | | 4/1977 | Eschmann |
| 4,129,127 A | | 12/1978 | Ellison |
| 4,454,873 A | * | 6/1984 | Laufenberg et al. .......... 128/90 |
| 4,683,877 A | | 8/1987 | Ersfeld et al. |
| 5,228,164 A | | 7/1993 | Graf et al. |
| 5,514,080 A | | 5/1996 | Blott et al. |
| 6,083,442 A | * | 7/2000 | Gabilly ...................... 264/163 |

\* cited by examiner

Primary Examiner—Allan R. Kuhns
(74) Attorney, Agent, or Firm—Dorsey & Whitney LLP; Robert B. Chickering

(57) ABSTRACT

Custom molded orthopedic impression shirt (27, 47) having a configuration substantially covering the torso of a patient. The impression shirt is formed from a thin, resin-impregnated elastic fabric shirt layer (27) mounted over a thin, flexible, resin-impervious release shirt layer (25), and preferably over a thin, elastic, thermally insulating fabric shirt layer (23). In the present method, the impression shirt is hardened on the patient's torso, cut off the patient's torso and then used to form a custom thoracic lumbar sacral orthosis in a fabrication laboratory.

4 Claims, 2 Drawing Sheets

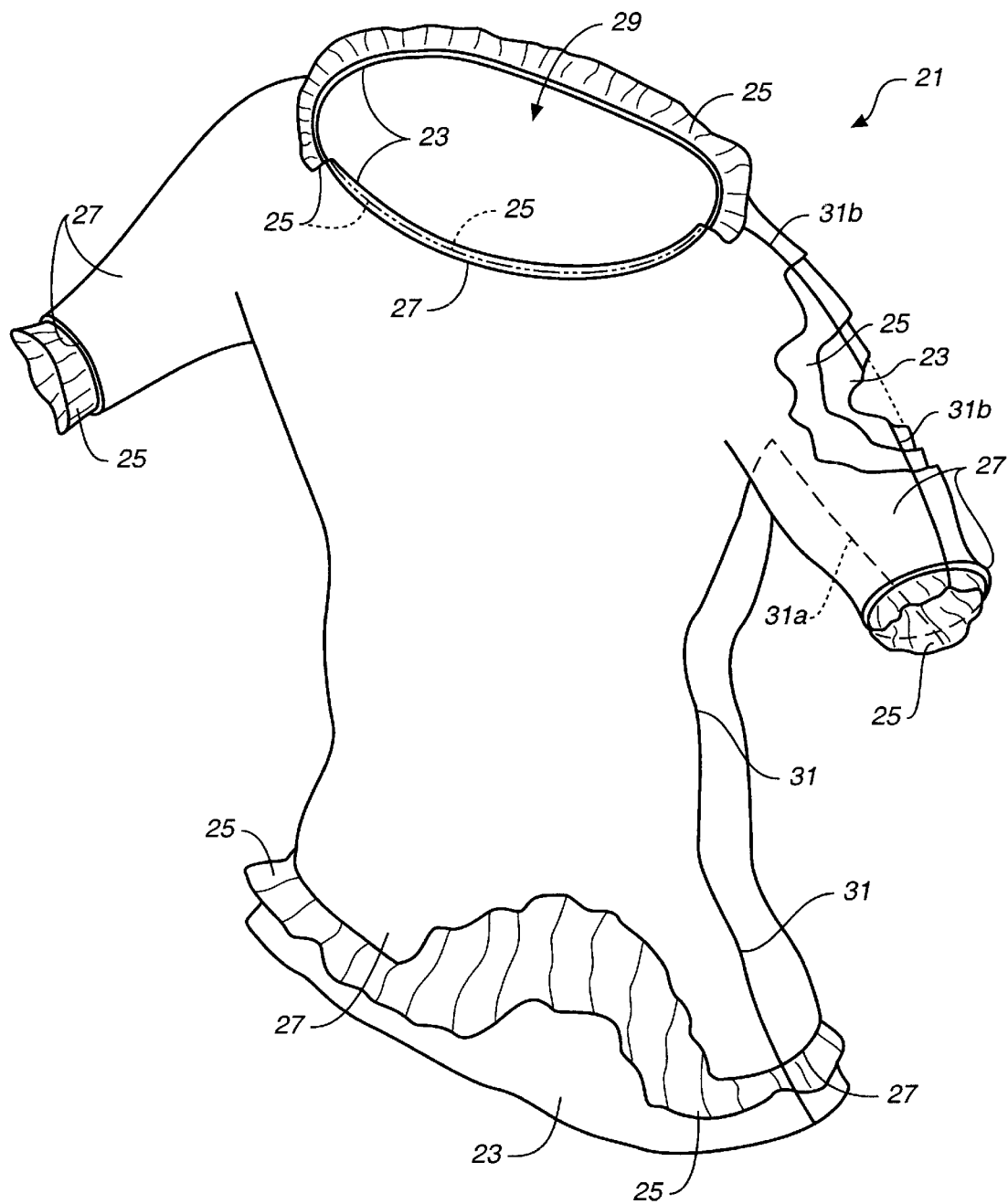
FIG._1

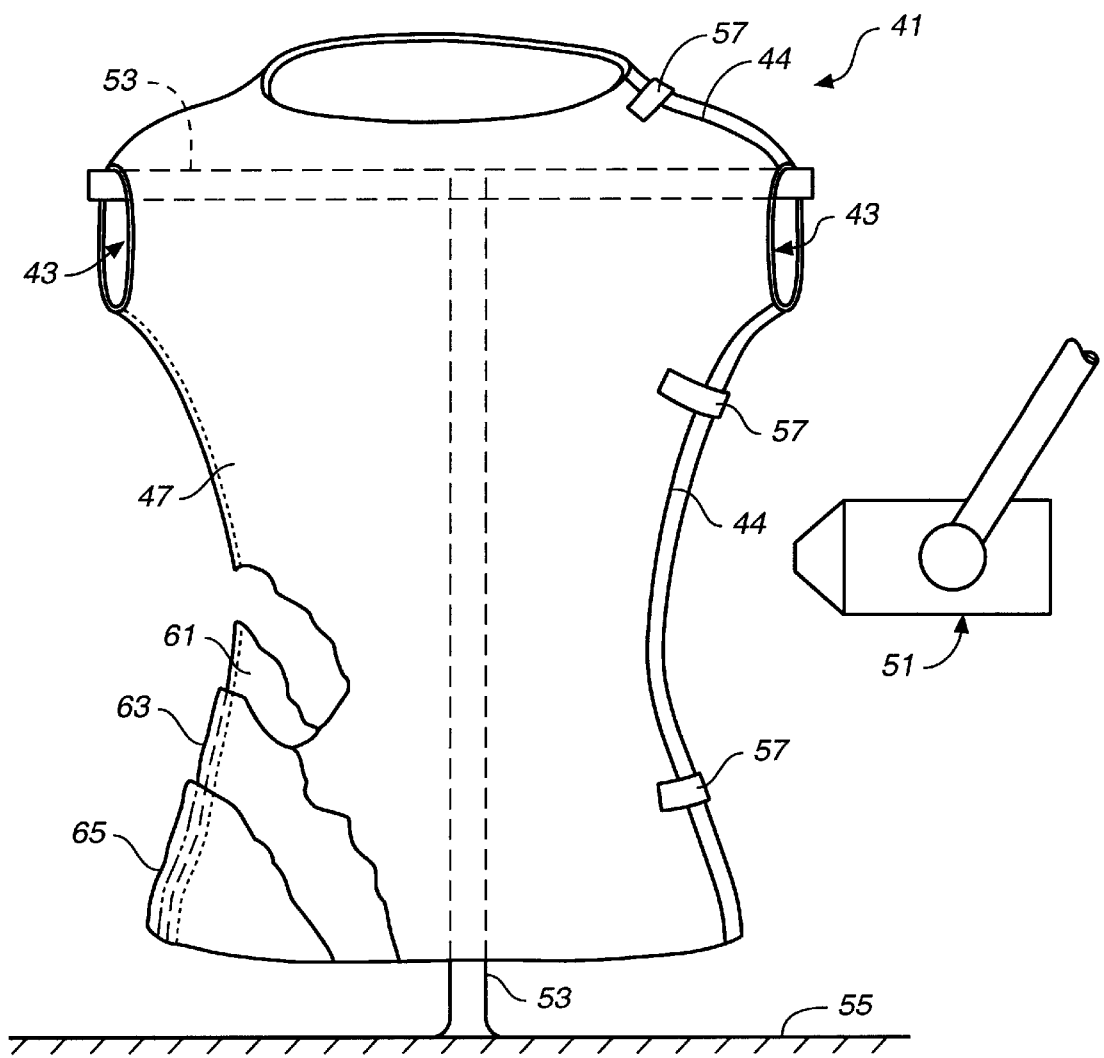
FIG._2

CUSTOM MOLDED ORTHOPEDIC IMPRESSION SHIRT, KIT AND METHOD

TECHNICAL FIELD

This invention relates, in general to custom molded thoracic lumbar sacral orthosis (orthopedic braces), and more particularly, relates to methods and apparatus for formation of a custom molded impression of a patient's torso which can subsequently be used to form an immobilization cast or torso brace.

BACKGROUND ART

Considerable effort has been directed toward the formation of orthopedic immobilizing casts or braces for various portions of patients' anatomies, most usually limbs. To the extent that casts or braces are formed for limbs, or even for a patient's torso, the cast and/or brace must be sufficiently rigid to support and/or immobilize the portion of the patient to which the cast is applied. This, in turn, usually requires that casts or braces be formed of a multiplicity of layers of material to provide the necessary strength and rigidity for immobilization or substantial weight support.

Typical of the prior art multi-layered casting systems are the orthopedic casts shown in U.S. Pat. Nos. 5,514,080; 4,683,877; 4,129,127; 4,019,506; and 3,656,475. Since these systems employ multiple layers and various combinations of hardening materials, they are tedious and difficult to form on the patient in order to achieve the highly desirable custom fit. Such custom casting, it will be understood, is often undertaken when the patient is in pain or experiencing considerable discomfort, making the construction of a cast in situ a disagreeable experience. Morever, part of a casting process often requires that a patient be held or maintained in a desired position during casting so that the eventual cast will support the patient as needed.

As the casting time becomes longer due to the complexity of forming a cast with sufficient rigidity to support the patient, it is more difficult to maintain the desired patient orientation or positioning.

Since in situ casting is often accomplished using resins which produce considerable heat during rigidification, another problem is providing sufficient thermal insulation between the patient and the various casting layers, which can contain a substantial volume of resin. Many casting resins experience exothermic curing. The thermal insulation required to withstand exothermic resin curing again makes the process of in situ casting more complex and tedious, as well as interposing layers between the patient and the eventual rigid cast which can affect cast fit.

Accordingly, it is an object of the present invention to provide a custom molded orthopedic impression shirt that can be used to mold an impression of a patient's torso from which custom, rigid, immobilizing or supporting thoracic lumbar sacral orthosis can be made in the laboratory.

A further object of the present invention is to provide a molded orthopedic impression shirt, and kit for forming the same, which can be used to form an impression of a patient's torso in a relatively short period of time.

A further object of the present invention is to provide a kit for and a method of forming, a custom molded orthopedic impression shirt that requires the use of minimal resin and the generation of minimal heat during the in situ molding process.

A further object of the present invention is to provide a method of forming a custom molded orthopedic impression shirt, and kit therefore which can be easily used by medical technicians with minimal training.

Still a further object of the present invention is to provide a custom molded orthopedic impression shirt and method which are suitable for scanning to enable the subsequent formation of an immobilizing or weight supporting thoracic lumbar sacral orthosis in a laboratory setting.

Still a further object of the present invention is to provide a custom molded orthopedic impression shirt, and method for formation of the same which can act as a base for a multi-layered immobilization or support cast or brace that is formed in the laboratory after the impression is taken.

The custom molded orthopedic impression shirt, method and kit of the present invention have other objects and features of advantage which will become apparent from, or are set forth in more detail in, the accompanying drawing and the following description of the Best Mode of Carrying out the Invention.

DISCLOSURE OF INVENTION

The method of forming a custom molded orthopedic impression shirt of the present invention comprises, briefly, the step of mounting a thin, flexible, resin-impervious release shirt or layer on the patient's torso. Alternatively, the release shirt or layer may be mounted under or over a thin elastic, thermally insulating, shirt or layer which is mounted on the patient's body. The method further includes the steps of mounting a resin-impregnated, thin, elastic, fabric impression shirt on the patient's torso over substantially the entire release shirt and thermal insulating layer, if there is one. The fabric impression shirt has sufficient elasticity to conform the release shirt, the insulating shirt and the impression shirt itself to the patient's torso. Finally, the method includes the steps of hardening the resin in the insulating shirt while mounted on the patient's torso and removing the hardened impression shirt from the patient's torso.

The present method further preferably includes the step of removing the hardened impression shirt by cutting the hardened impression shirt and release shirt and insulating fabric shirt along a side of the impression shirt and resiliently outwardly displacing the cut hardened impression shirt to enable removal from the patient's torso. Finally, the method may include the steps of scanning the hardened impression shirt to obtain digital data corresponding to the shape of the impression shirt, and making a thoracic lumbar sacral orthosis based upon the scanned digital data. In an alternative aspect of the method of the present invention, the hardened impression shirt is used as a base, when removed from the patient, to enable formation of the orthosis over the impression shirt, either by casting the orthosis on a positive made from the impression shirt, or layering reinforcing materials over the impression shirt.

In another aspect of the present invention a kit for forming a custom molded orthopedic impression shirt is provided which comprises, briefly, a fabric impression shirt having a configuration substantially covering the torso of a patient and having sufficient elasticity and being sufficiently thin to enable formation of a shell conforming to the patient's torso which is suitable for scanning, casting or reinforcing to manufacture a thoracic lumbar sacral orthosis once the impression shirt is removed from the patient's torso. The kit also includes a quantity of curable resin, preferably impregnated in the impression shirt, sufficient to rigidify the impression shirt.

BRIEF DESCRIPTION OF THE DRAWINGS

FIG. 1 is a top pictorial schematic view of a custom molded orthopedic impression shirt, partially broken away, and constructed in accordance with the present invention.

FIG. 2 is a side elevation view of an alternative embodiment of the orthopedic impression shirt of the present invention removed from the patient's torso and supported for scanning, casting or layering up of a thoracic lumbar sacral orthosis.

BEST MODE OF CARRYING OUT THE INVENTION

The orthopedic impression shirt, method and kit of the present invention employ the general approach of attempting to minimize the time, heat generation and a number of components used to form a custom molded orthopedic torso impression on the patient's body. Rather than attempting to layer up sufficient layers of material so as to make thoracic lumbar sacral orthosis (a brace or cast) in situ having sufficient strength to support or immobilize the patient, the method, kit and shirt of the present invention form a hardened impression shell, which is not suitable for direct use as an orthosis, and the hardened shell is removed from the patient and then used in the laboratory to form a custom thoracic lumbar sacral orthosis.

Referring now to FIG. 1, a custom molded orthopedic impression shirt, generally designated 21, is shown. While three layers of material are shown in FIG. 1, only two layers are required in the broadest aspect of the present invention, as will be set forth below. Each layer most preferably is provided as a shirt.

The innermost layer or shirt may be either a thin, flexible, resin-impervious release layer or a thin, elastic, thermally insulating fabric layer. If the release layer is thick enough to provide thermal insulation, the thermally insulating layer can be eliminated. As shown in FIG. 1, however, three layers are provided, and layer 23 next to the patient's torso can be either the thermally insulating layer or the release layer, with layer 25 being the other of the two choices. It will be assumed for purposes of discussion that layer or shirt 23 is a relatively thin, double knit nylon fabric thermally insulating layer having substantial elasticity so that it will conform closely to the patient's body.

One of the important aspects of the present invention is that the resin-impregnated outer shirt or layer is also relatively thin, and therefore, a lesser amount of curable resin is employed than when a strong multi-layer cast or brace is molded on the patient's body using resins. Most resins employed in current orthopedic casting techniques involve exothermic reactions in order to produce hardening of the casting resin. That also is preferred in the present invention, but the amount of resin can be reduced, since an impression, not an orthosis, is being produced. The amount of exothermic heat generated in the present method is, therefore, reduced.

Accordingly, fabric thermal insulating layer 23 can be thin and need only provide minimal thermal insulation so as to avoid patient discomfort, which may be heightened if the impression is being formed soon after a surgical procedure or injury to the patient.

Mounted over thermally insulating shirt 23 is a thin, flexible, resin-impervious release layer or shirt 25. Release shirt 25 can be provided by any number of plastic materials which will not bond to, or be destroyed by, the resin used in the outermost layer of the assembly. For example, resin-impervious release layer 25 can be as little as 0.005 inches in thickness and be formed of polyethylene. It will be understood that even a thin layer 25 will add to the thermal insulation between the exothermic curing of the resin and the patient. In fact as noted above, innermost shirt 23 of thermally insulating fabric could be eliminated in favor of a thicker release shirt 25 in the broadest aspect of the present invention. Since most release layers or shirts will be impervious to the passage of air moisture, an additional advantage of mounting thermal insulating layer 23 under release layer or shirt 25 is that insulating layer 23 will breathe and therefore be more comfortable against the patient's skin than would be an elastomeric shirt 25. Nevertheless, in an alternative form of the present invention the release layer or shirt is the innermost shirt 23 and the thermally insulating layer is provided by shirt or layer 25.

Positioned over layer or shirt 25 is a resin-impregnated, thin, elastic fabric impression shirt 27. Impression shirt 27 should have sufficient elasticity to conform shirt 25 and shirt 23 to the patient's torso. Since the thermally insulating shirt is also preferable elastic, and since the release shirt or layer is very thin and pliable, the primary need for elasticity of impression shirt 27 is so that the elasticity will be sufficient to cause conformation of the impression shirt to the patient's torso.

It is preferably that all three layers, namely, layer 23, layer 25 and impression shirt 27, have a shirt-like. constructions so that each layer is substantially wrinkle free when placed on the patient's torso. Each shirt can be sleeved or sleeveless, as can be seen by comparing FIGS. 1 and 2. FIG. 1 shows a sleeved embodiment and FIG. 2 shows a sleeveless embodiment. Most preferably neck opening 29 in outermost fabric impression shirt 27 is relatively large so that it can easily pass over the patient's head. The various layers or shirts can be manufactured in various sizes, and the casting technician can select shirts which closely match the size of patient's torso.

In use, one of the release shirt and the thermally insulating shirt can be placed over the patient's head and onto his or her torso and manually conformed to the patient's torso. Since neither the release layer nor the thermally insulating layer are resin-impregnated, they can have a relatively small neck opening. Next, the other of the release shirt and thermally insulating shirt can be placed over the patient's torso and smoothed so as to minimize wrinkles. Again the release shirt and thermally insulating shirt can have arms, a neck portion and waist portion which extends downwardly beyond that which the final impression shirt reaches. As seen in FIG. 1, the release layer or shirt, shown as 25, extends beyond molding or impression shirt 27 at the arms, neck and waist.

Finally, thin, elastic, fabric impression shirt 27 is mounted over the patient's torso and the two inner shirt layers 25 and 23. Shirt 27 most preferably is formed from a woven knit synthetic yarn with elastomeric fibers exhibiting extensibility of about 100 percent in a direction transverse to a longitudinal axis of the patient's torso. In the most preferred form, the fabric impression shirt initially is saturated/impregnated with a curable resin of a type which is set forth herein below. Since the fabric impression shirt is elastic and flexible, it can be rolled up from the waist to a position just under the arms, if shirt 27 has arms, with the curable resin carried by the rolled up fabric shirt 27. Enlarged neck opening 29 and the relatively large opening at the waist of the resin-impregnated shirt allows the same to be placed over the patient's head with minimal contact of the resins with the patient. Patient contact can be reduced further by providing the patient with a disposable shower cap-like protective envelope for the patient's head. Similarly, the patient's arms can be protected by disposable gloves which extend up to release shirt 25. The protective gloves and shower cap envelope can be removed once the resin-saturated/impregnated elastic fabric impression shirt is positioned over the patient's head and his arms are inserted through the sleeves, or for sleeveless models, through the sleeve openings.

Once the arms are positioned in the sleeves or arm hole openings, the lower portion of impression shirt 27 can be rolled down on the patient's torso to the position shown in FIG. 1 proximate the patient's waist. The casting technician can then smooth and conform the elastic compression shirt to the patient's torso while the resin is in an uncured condition. The elasticity of the shirt combines with manual smoothing by the technician to allow the shirt to conform closely to the patient's torso and upper arms (for sleeved shirts). The preferred form of resin for use with the impression shirt of the present invention is a water-curable resin such as a water-curable, isocyanate-functional prepolymer. Elastic impression shirt 27 may be formed using fabrics and resins which are set forth in more detail in U.S. Pat. No. 5,228,164, which is incorporated herein by reference.

Once the technician has smoothed the impression shirt down over the patient's torso, water can be applied to the shirt using a spray bottle or other water applicator so as to cause the resin to begin curing. Before starting the curing process, or soon after it has been started, the technician will position the patient's torso in a desired orientation for formation of the impression. If there is a posture in which the eventual thoracic lumbar sacral orthosis is to support the patient, that posture need only be maintained during the curing stage, which can be relatively short because the quantity of resin on the impression shirt layer 27 is relatively small and shirt 27 itself is relatively thin. Thus, in as little as 4–6 minutes, the impression shirt will be sufficiently hard so as to be self supporting. This means that the patient need no longer be tediously held or positioned in the desired posture, and the impression shirt will start to provide some support for the patient in the desired posture as it cures.

If the thermal insulating layer is underneath the release layer, the thermal insulating layer will not bond to impression shirt layer 27. If thermal insulating layer is provided as shirt or layer 25, it will bond to the resin-saturated/impregnated impression shirt layer 27 during hardening of the resin.

The next step in the method of the present invention is to remove the impression shirt from the patient. This can be accomplished by cutting the hardened impression shirt layer 27, release shirt layer and insulating fabric shirt layer along a side of the molded or hardened assembly, for example, as shown at cut line 31. Cut line 31 preferably comes outwardly from under the arm to the edge of the shirt sleeve, in a manner shown in dotted lines 31a in FIG. 1, and then continues on the upper side of the arm at 31b up to neck hole 29. The release or cut line 31, 31a, 31b allows all three shirt layers to be resiliently outwardly displaced once the impression shirt is hardened to enable the hardened shirt assembly to be removed from the patient. In sleeved versions, the opposite arm may also need to be cut proximate its opening to facilitate easy release from the patient's other arm.

Having removed all three shirt layers from the patient, the patient is no longer involved in the process of making a custom molded thoracic lumbar sacral orthosis which is suitable for immobilizing or supporting the patient. Shirt layer 23 and layer 25 can both be removed from inside the hardened impression shirt layer 27, if layer 25 is the release layer and layer 23 the insulating layer. If these layers are reversed only innermost shirt 23, the release shirt, can be removed. In either case the result is a hardened thin shell of uniform thickness which now can be used to form a thoracic lumbar sacral orthosis (orthopedic torso brace or orthopedic cast) in the laboratory.

Referring now to FIG. 2, use of the hardened impression shirt to form an orthosis can be described in more detail. A modified form of the impression shirt, generally designated 41, is shown in which only the outer hardened shirt layer 47 is present, and the shirt illustrated in FIG. 2 is sleeveless, having arm holes 43 instead of sleeves.

The hardened impression shirt or shell 41 can be used in a number of different ways to form orthosis. One approach is to scan impression shirt 47, which is schematically illustrated by digital scanner 51. Digital scanner 51 can be used to scan the outside of the impression shirt, as shown in FIG. 2, or to scan the inside of the shirt. The shirt will be mounted on a fixture 53 from a support surface 55 so as to orient the same at a predetermined known orientation relative to scanner 51. Various types of fixtures 53 can be employed, depending upon whether or not inside scanning or outside scanning will be used. Since the torso shell 47 is thin and uniform in thickness, scanning on the outside and digital removal of the known thickness of the shell can be used to obtain digital data as to the inside surface, as it was custom molded to the patient's body. Cut line 44 can be secured back together by fasteners, such as tape 57 or adhesives. Impression scanning equipment are well known in the orthopedic industry for capturing sufficient digital data to enable creation of an orthosis from impression shirt 47. The scanned data also can be digitally adjusted to accommodate an orthosis liner or padding on the inside of the orthosis.

Another approach to forming thoracic lumbar sacral orthosis from hardened impression shirt 47 would be to fill the inside of shirt 47 with a supporting foam or plaster of Paris and then form the orthosis over a part or all of the supported torso shell 47. The thin nature of shell 47 allows the orthosis formed over it to be only slightly padded, which is desirable in any event, in order to produce a close custom fit.

An additional approach to making a thoracic lumbar sacral orthosis using a hardened impression shirt 47 is to essentially build the orthosis over impression shirt 47. Thus, a liner or padding layer 61 could be placed inside hardened shirt shell 47, and reinforcing layers 63 and 65 placed over impression shirt 47. The outer layers 63 and 65 can have substantial strength and include, for example, substantial quantities of resin, heavy fabrics and even reinforcing plates or the like. Since this work is done in a laboratory, there is no problem with exothermic reactions being uncomfortable for the patient or in connection with positioning of reinforcing layers and materials in the cast, which would be tedious if the patient had to maintain a desired orientation or posture.

Finally, shell 41 also can be used to make a positive mold inside the shell, for example by using plaster of Paris. The shell can be reinforced exteriorly while the positive is made so as to maintain the molded dimensions, and then shell 41 is removed from the cast positive. An orthosis is then formed over the positive mold in the laboratory.

Thus, the present invention allows a hardened impression shirt to be used as a shell for the formation of custom molded thoracic lumbar sacral orthosis in the laboratory. The present method also can be used with, or incorporate, auxiliary attachments or immobilizing structures, such as neck, lower limb and upper limb supports.

What is claimed is:
1. A method of forming a custom molded orthopedic torso impression shirt comprising the steps of:

mounting a thin, flexible, resin-impervious release layer over an area of a patient's torso to be molded;

mounting a resin-impregnated, thin, elastic, fabric impression shirt on the patient's torso over substantially the entire release layer, said fabric impression shirt conforming said release layer to the patient's torso over the area;

hardening a resin in said impression shirt while mounted on the area of the patient's torso;

removing the hardened impression shirt from the area of patient's torso by cutting the hardened impression sheet and release layer along a side of the impression shirt;

resiliently outwardly displacing the cut hardened impression shirt in a manner enabling removal thereof from the patient;

scanning said hardened impression shirt to obtain digital data corresponding to the shape of said hardened impression shirt; and making a thoracic lumbar sacral orthosis based upon said digital data.

2. A method of forming a custom molded orthopedic torso impression shirt comprising the steps of:

mounting a thin, flexible, resin-impervious release layer over an area of a patient's torso to be molded;

mounting a resin-impregnated, thin, elastic, fabric impression shirt on the patient's torso over substantially the entire release layer, said fabric impression shirt conforming said release layer to the patient's torso over the area;

hardening a resin in said impression shirt while mounted on the area of the patient's torso;

removing the hardened impression shirt from the area of patient's torso by cutting the hardened impression sheet and release layer along a side of the impression shirt;

resiliently outwardly displacing the cut hardened impression shirt in a manner enabling removal thereof from the patient; and after said displacing step, making a thoracic lumbar sacral orthosis supported on said hardened impression shirt.

3. A method of forming a custom molded orthopedic torso impression shirt comprising the steps of:

mounting a thin, flexible, resin-impervious release layer over an area of a patient's torso to be molded;

mounting a resin-impregnated, thin, elastic, fabric impression shirt having shoulder-covering connecting shirt portions between a front shirt portion and a back shirt portion of said impression shirt on the patient's torso over substantially the entire release layer, said fabric impression shirt conforming said release layer to the patient's torso over the area;

hardening a resin in said impression shirt while mounted on the area of the patient's torso; and removing the hardened impression shirt from the area of patient's torso.

4. A method of forming a custom molded orthopedic torso impression shirt comprising the steps of:

mounting a thermally insulating fabric layer over the torso and upper arms of a patient;

mounting a thin, flexible, resin-impervious release layer over an area of a patient's torso and upper arms to be molded;

mounting a resin-impregnated, thin, elastic, fabric impression shirt having sleeves thereon on the patient's torso and upper arms over substantially the entire thermally insulating fabric layer and release layer, said fabric impression shirt conforming said release layer to the patient's torso and upper arms over the area;

hardening a resin in said impression shirt while mounted on the area of the patient's torso; and removing the hardened impression shirt from the area of patient's torso.

* * * * *